United States Patent [19]

Koziol et al.

[11] Patent Number: 4,615,702
[45] Date of Patent: Oct. 7, 1986

[54] INTRAOCULAR LENS AND METHOD OF FORMING THE LENS

[76] Inventors: Jeffrey E. Koziol, 601 W. Central, Mount Prospect, Ill. 60056; Gholam A. Peyman, 535 N. Michigan Ave., Chicago, Ill. 60611

[21] Appl. No.: 648,600
[22] Filed: Sep. 10, 1984
[51] Int. Cl.⁴ ............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 2,834,023 | 5/1958 | Lieb | 623/6 |
| 4,073,014 | 2/1978 | Poler | 623/6 |
| 4,159,546 | 7/1979 | Shearing | 623/6 |
| 4,168,547 | 9/1979 | Konstantinou et al. | 623/6 |
| 4,172,297 | 10/1979 | Schlegel | 623/6 |
| 4,206,518 | 6/1980 | Jardon et al. | 623/6 |
| 4,242,760 | 1/1981 | Rainin | 623/6 |
| 4,253,200 | 3/1981 | Kelman | 623/6 |
| 4,257,130 | 3/1981 | Bayers | 623/6 |
| 4,363,143 | 12/1982 | Callahan | 623/6 |

FOREIGN PATENT DOCUMENTS

| | | | |
|---|---|---|---|
| 2114315 | 8/1983 | United Kingdom | 623/6 |
| 2124500 | 2/1984 | United Kingdom | 623/6 |

Primary Examiner—Richard J. Apley
Assistant Examiner—James Prizant
Attorney, Agent, or Firm—Roylance, Abrams, Berdo & Goodman

[57] ABSTRACT

An intraocular lens formed of a soft, resilient polymeric optical element and a resilient polymeric support having an annular portion embedded in the optical element and a pair of mounting arms extending outwardly of the optical element. The optical element and support can be folded for insertion into the eye via a small incision. The support is embedded in the optical element during molding and polymerization of the optical element.

10 Claims, 6 Drawing Figures

INTRAOCULAR LENS AND METHOD OF FORMING THE LENS

FIELD OF THE INVENTION

The invention relates to intraocular lenses. The lens comprises a soft, resilient polymeric optical element and a resilient polymeric support embedded therein and having outwardly extending mounting arms. The support is embedded in the optical element during molding of the optical element.

BACKGROUND OF THE INVENTION

Artificial intraocular lenses, used to replace damaged or diseased natural lenses in the eye, have been widely used in the last several years. Typically, such artificial intraocular lenses comprise some type of optical element and a support coupled to the element for positioning the optical element in the proper location in the eye.

These lenses have typically included hard polymeric or glass optical elements with metallic or polymeric supports. One problem with hard lenses is that the incision in the eye to insert them must be at least as large as the diameter of the optical portion of the lens. Thus, the patient must experience a fairly traumatic large incision.

Use of soft, foldable polymeric lenses is hampered because it is difficult to support them and it is difficult to insert them into the eye.

Another problem involving either hard or soft intraocular lenses is the need for adhesives or extra, complicated steps to connect the supports to the optical element.

Thus, there is a continuing need for improvement in intraocular lenses.

Examples of such prior art intraocular lenses are disclosed in the following U.S. patents: U.S. Pat. Nos. 2,834,023 to Lieb; 4,159,546 to Shearing; 4,172,297 to Schlegel; 4,206,518 to Jardon et al; 4,242,760 to Rainin; 4,253,200 to Kelman; 4,257,130 to Bayers; and 4,363,143 to Callahan.

SUMMARY OF THE INVENTION

Accordingly, a primary object of the invention is to provide an intraocular lens having a soft, resilient optical element and a resilient support, both of which are foldable for easy insertion into the eye via a small incision, and having a support more rigid than the optical element to ease insertion and to prevent collapse or distortion of the optical element after insertion into the eye.

Another object of the invention is to provide such an intraocular lens that avoids the use of adhesives or numerous steps to couple a support to the optical element.

Another object of the invention is to provide an intraocular lens that is comprised of a soft, resilient polymeric optical element and a resilient polymeric support embedded therein during molding of the optical element.

The foregoing objects are basically attained by providing a method of making an intraocular lens comprising the steps of forming a resilient support including an annular portion and mounting arms, positioning a portion of the support in a mold, molding an optical element in the mold including introducing material forming the optical element into the mold in liquid form and surrounding the portion of the support in the mold with such material forming the optical element, converting the material forming the optical element from liquid form into solid form, and removing the intraocular lens formed by the support and the optical element from the mold.

The foregoing objects are also attained by providing an intraocular lens comprising a resilient optical element; and a resilient support having an annular portion and mounting arms, the annular portion being embedded in and surrounded by the material forming the optical element, the mounting arms extending outwardly of the material forming the optical element.

Other objects, advantages and salient features of the present invention will become apparent from the following detailed description, which, taken in conjunction with the annexed drawings, discloses a preferred embodiment of the present invention.

DRAWINGS

Referring now to the drawings which form a part of this original disclosure:

DETAILED DESCRIPTION OF THE INVENTION

Figure 3:
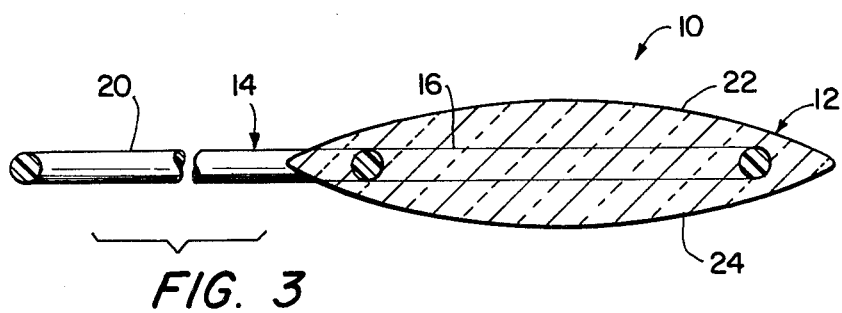
FIG. 3 is an enlarged right side elevational view in section of the intraocular lens in accordance with the invention taken along line 3—3 in FIG. 1.
Figure 4:
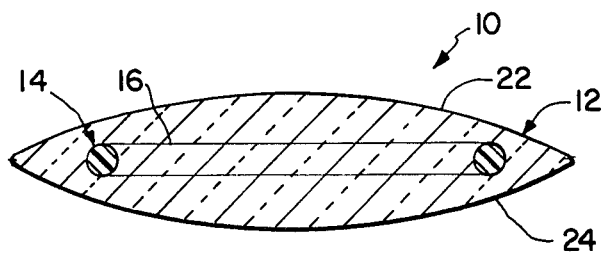
FIG. 4 is a front elevational view in section taken along line 4—4 in FIG. 1 showing a portion of the support embedded in and surrounded by the optical element.
Figure 5:
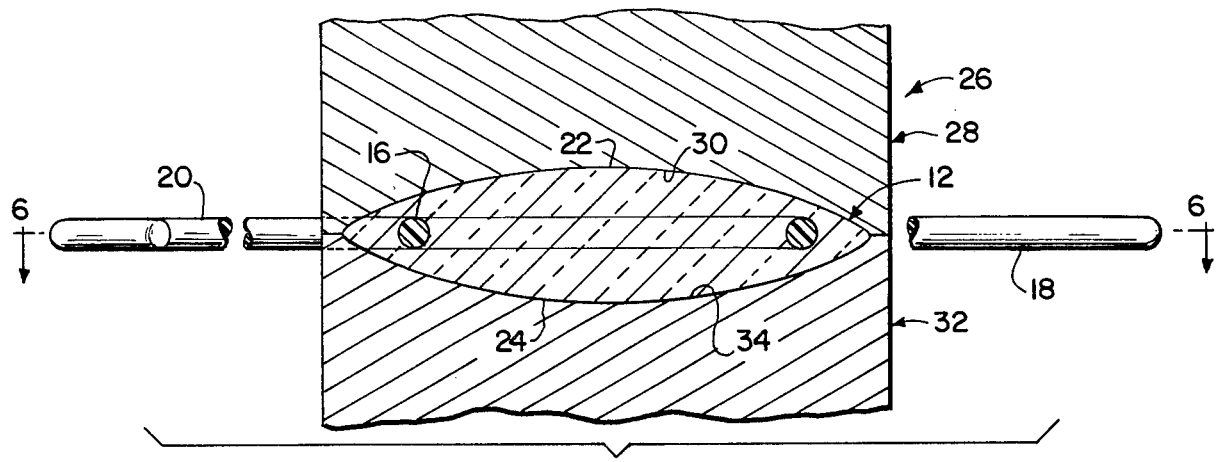
FIG. 5 is a side elevational view, in partial section, of the support having a portion located in a mold and the optical element surrounding that portion of the support in the mold.
Figure 6:
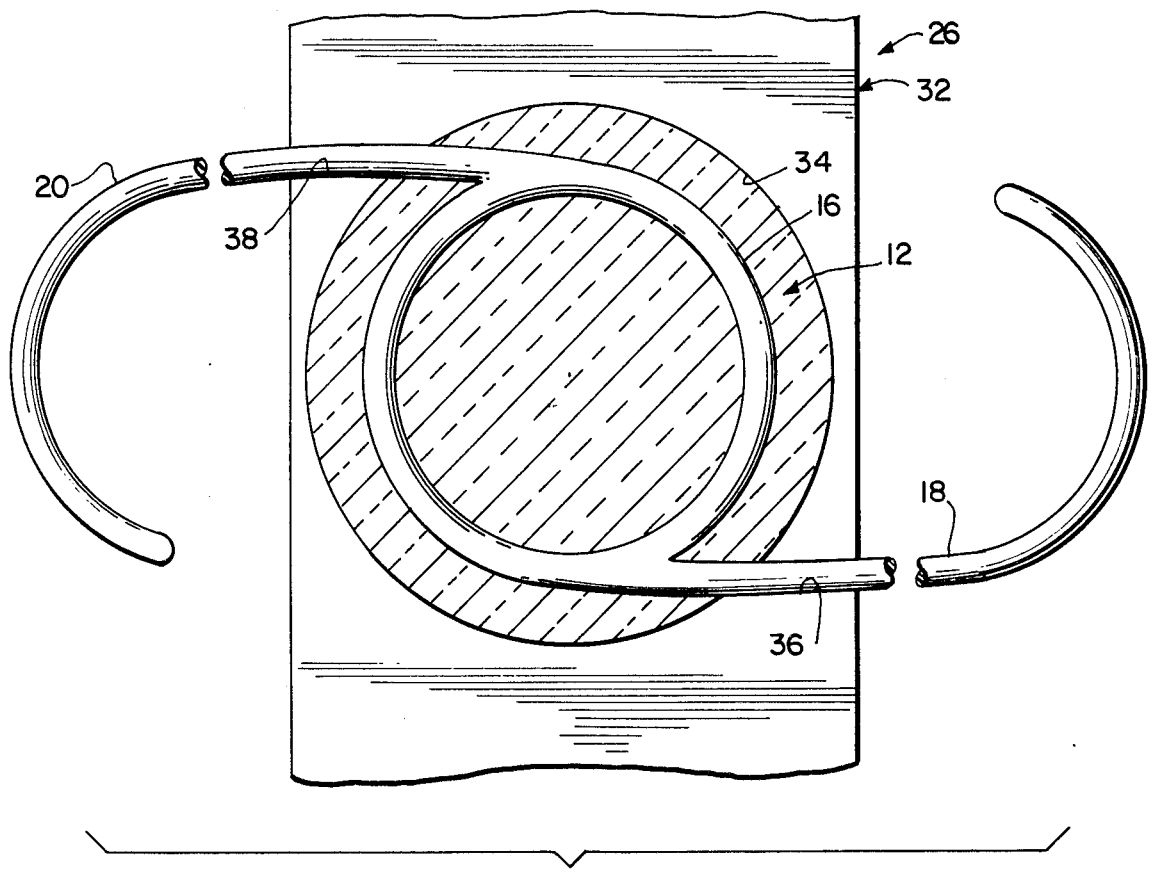
FIG. 6 is a top elevational view in section taken along line 6—6 of FIG. 5 showing the bottom half of the mold as well as the optical element and the support.

Referring now to FIGS. 1–4, the intraocular lens 10 in accordance with the invention comprises a soft transparent optical element 12 and a support 14, both of which are flexible and resilient, and therefore bendable or foldable. As seen in FIGS. 3 and 4, a portion of the support is embedded in and surrounded by the optical element. This is accomplished by inserting a portion of the support in a mold and molding the optical element around that portion of the support, as seen in FIGS. 5 and 6. The support is more rigid than the optical element to provide the necessary structural suspension of the optical element when placed in the eye.

The support 14 comprises an annular portion 16 and a pair of curved mounting arms 18 and 20 rigidly coupled thereto and extending initially substantially tangentially thereof on diametrically opposed sides. The arms and annular portion are coplanar, although the tips of the arms can be bent out of the plane of the arms and annular portion to provide for better connection in the eye. Advantageously, the support is about 13 millimeters long and the annular portion 16 is about 5.5 millimeters in diameter. In cross section, the support material is circular. The thickness of the material forming the annular portion and mounting arms is preferably uniform and advantageously about 0.2 to 0.3 millimeters in diameter.

As seen in FIGS. 1-4, the support 14 is a one-piece molded member; although it is possible to form the support member by rigidly attaching, in a suitable manner such as by adhesives or fusion, the mounting arms to the annular portion. Advantageously, the entire support is formed from polymeric material such as tetrafluoroethylene. Alternatively, the support could be formed of metal such as stainless steel.

Since the optical element is made of soft polymeric material and therefore cannot support itself, the support is advantageously more rigid than the optical element, yet flexible and bendable. The melting point of the material forming the support is higher than the elevated temperatures used to polymerize the material forming the optical element, as will be described hereinafter.

Figure 1:
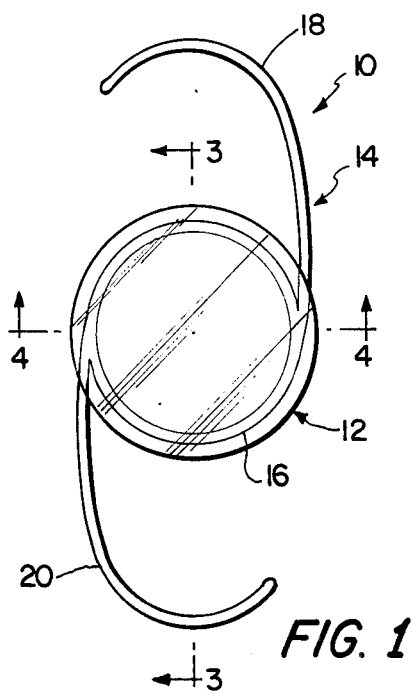
FIG. 1 is a top plan view of the intraocular lens in accordance with the invention including an optical element and a support embedded therein.
Figure 2:
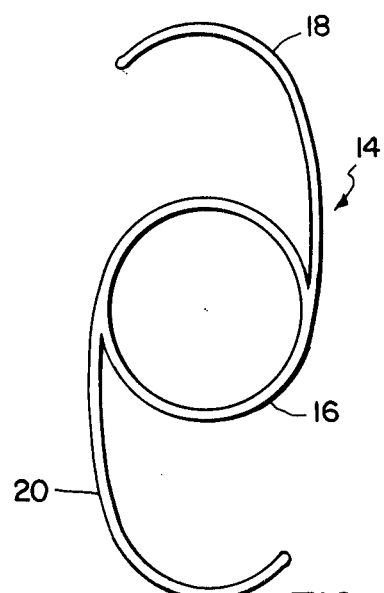
FIG. 2 is a top plan view of the support for the optical element including an annular portion and a pair of mounting arms, without the optical element coupled thereto.

The optical element 12, as best seen in FIGS. 1 and 3-4, is circular in plan view, is transparent and comprises a first surface 22 and a second surface 24, each of which is convex. The optical element is advantageously molded as one piece onto and around the annular portion 16 and part of the mounting arms 18 and 20 so that such a portion of the support is surrounded by and embedded in the material forming the optical element.

Advantageously, the optical element is formed from a monomer formulation resulting in a silicone elastomer upon polymerization. Examples of such monomers are: hexamethyl-cyclotrisiloxane, octamethyl-cyclotetrasiloxane, decamethyl-cyclopentasiloxane, octaphenylcyclo-tetrasiloxane, diphenylsilane-diol, trimethyltriphenyl-cyclotrisiloxane, vinylmethyl-cyclosiloxanes, trifluoropropylmethyl-cyclosiloxanes, methylhydro-cyclosiloxane, hexamethyl-disiloxane, divinyltetramethyldisiloxane and tetramethyl-disiloxane. Polymerization takes places for one to two hours at a temperature of 60°-200° C.

As seen in FIGS. 3 and 4, the support 14 is essentially centrally located in the optical element 12 equidistant from the first and second convex surfaces 22 and 24 and equally radially spaced from the outer periphery of the optical element.

As seen in FIGS. 5 and 6, a mold 26 is used to form the intraocular lens 10 and comprises an upper part 28 with an upper concave cavity 30 and a lower part 32 with a lower concave cavity 34. The upper and lower parts of the mold are relatively movable towards and away from each other in order to insert the support therein, introduce material forming the optical element therein, and remove the combined optical element and support once the intraocular lens is fully formed. As seen in FIG. 6, the lower part 32 of the mold has a pair of slots 36 and 38, which are semi-cylindrical in cross section, for the reception of the mounting arms in the support. Similar slots, not shown, are also found in the upper part of the mold.

Thus, in forming the intraocular lens 10 in accordance with the invention, the mold parts are opened, and then the support 14 is positioned in the mold so that the annular portion 16 and part of the arms are located in the lower cavity 34 as seen in FIG. 6.

Then, a monomer formulation in liquid form, having a volume somewhat greater than that of the two cavities, is introduced into the lower mold cavity and the mold is closed with the excess volume leaking out between the mold parts. The mold is then heated for a predetermined time at an elevated predetermined temperature that will polymerize the monomers located therein into a solid polymer. As seen in FIGS. 5 and 6, when the material in liquid form is introduced into the mold, it surrounds the portion of the support located therein so that the support is ultimately embedded therein after polymerization.

Following polymerization of the optical element material, the mold is opened and the combined optical element and support are removed therefrom.

Rather than introducing the liquid monomers into an open mold and then closing the mold, the mold can be closed after insertion of the support and the monomers then can be injected into the mold under pressure via a suitable input port. Polymerization as described above then takes place.

As an alternative to silicone polymer, a hydrogel polymer can be used to form the optical element. This material is very hard when dry and becomes soft after it is hydrated. When this material is used, the mold need only encase the support in a block of the hydrogel polymer and, after removal from the mold, the block can be lathe cut to a precise optical shape.

While one advantageous embodiment has been chosen to illustrate the invention, it will be understood by those skilled in the art that various changes and modifications can be made therein without departing from the scope of the invention as defined in the appended claims.

What is claimed is:

1. An intraocular lens, the combination comprising:
   a soft, resilient optical element; and
   a resilient support having an annular portion and mounting arms,
   said annular portion being completely embedded in and completely surrounded by the material forming said optical element,
   said mounting arms being coupled to said annular portion and extending outwardly of the material forming said optical element.
2. An intraocular lens according to claim 1, wherein said support is integrally formed as one piece.
3. An intraocular lens according to claim 1, wherein said support is formed of polymeric material.
4. An intraocular lens according to claim 3, wherein said polymeric material is tetrafluoroethylene.
5. An intraocular lens according to claim 1, wherein said optical element is formed of polymeric material.
6. An intraocular lens according to claim 1, wherein said optical element is formed of silicone.
7. An intraocular lens according to claim 1, wherein said optical element is formed of polymeric material, and
   said support is formed of polymeric material.
8. An intraocular lens according to claim 1, wherein each of said mounting arms has a portion extending substantially tangentially of said annular portion.
9. An intraocular lens according to claim 8, wherein said annular portion and said mounting arms lie substantially in the same plane.
10. An intraocular lens according to claim 1, wherein said annular portion and said mounting arms lie substantially in the same plane.

* * * * *